(12) United States Patent
Linsley et al.

(10) Patent No.: US 6,232,068 B1
(45) Date of Patent: May 15, 2001

(54) MONITORING OF GENE EXPRESSION BY DETECTING HYBRIDIZATION TO NUCLEIC ACID ARRAYS USING ANTI-HETERONUCLEIC ACID ANTIBODIES

(75) Inventors: Peter S. Linsley, Seattle, WA (US); Patrick Baeuerle, Gauting (DE)

(73) Assignees: Rosetta Inpharmatics, Inc., Kirkland, WA (US); Tularik Inc., South San Francisco, CA (US)

( * ) Notice: Subject to any disclaimer, the term of this patent is extended or adjusted under 35 U.S.C. 154(b) by 0 days.

(21) Appl. No.: 09/236,139

(22) Filed: Jan. 22, 1999

(51) Int. Cl.[7] .............................. C12Q 1/68; G01N 33/53
(52) U.S. Cl. ................................................ 435/6; 435/7.1
(58) Field of Search .............................. 435/6, 701, 91.2

(56) References Cited

U.S. PATENT DOCUMENTS

| | | | |
|---|---|---|---|
| 4,732,847 | 3/1988 | Stuart et al. | 435/6 |
| 4,748,111 | * 5/1988 | Dattagupta et al. | 435/7 |
| 4,833,084 | 5/1989 | Carrico et al. | 435/240.27 |
| 4,865,980 | 9/1989 | Stuart et al. | 435/240.27 |
| 5,510,270 | 4/1996 | Fodor et al. | 436/518 |
| 5,556,752 | 9/1996 | Lockhart et al. | 435/6 |
| 5,578,832 | 11/1996 | Trulson et al. | 250/458.1 |
| 5,827,661 | * 10/1998 | Blais | 435/6 |
| 5,861,242 | * 1/1999 | Chee et al. | 435/5 |
| 5,919,626 | * 7/1999 | Shi et al. | 435/6 |

FOREIGN PATENT DOCUMENTS

WO 98/41531   9/1998 (WO) .

OTHER PUBLICATIONS

Baldwin et al. Monoclonal Antibodies for cancer detection and therapy, p. 20, 1985.*
Scott Trends in Biotechonolgy 3: 170–174, 1985.*
Blanchard et al., 1996, "High–density oligonucleotide arrays", Biosensors & Bioelectronics 11: 687–90.
Butzow et al., 1965, "Interactions of metal ions with polynucleotides and related compounds. IV. Degradation of polyribonucleotides by zinc and other divalent metal ions", Biopolymers 3:95–107.
Chee et al., 1996, "Accessing genetic information with high–density DNA arrays", Science 274:610–614.
Coutlée et al., 1991, "Immunodetection of DNA with biotinylated RNA probes: a study of reactivity of a monoclonal antibody to DNA–RNA hybrids", Anal Biochem 181:96–105.
DeRisi et al., 1996, "Use of a cDNA microarray to analyse gene expression patterns in human cancer", Nat Genet 14:457–460.
DeRisi et al., 1997, "Exploring the metabolic and genetic control of gene expression on a genomic scale", Science 278:680–686.
Digene, Beltsville, MD, company and product information obtained from www.digene.com.
Fliss et al., 1993, "Production and characterization of anti–DNA–RNA monoclonal antibodies and their application in Listeria detection", Appl Environ Microbiol 59:2698–2705.
Fodor et al., 1991, "Light–directed, spatially addressable parallel chemical synthesis", Science 251:767–773.
Goffeau et al., 1996, "Life with 6000 genes", Science 274:546, 563–567.
Lashkari et al., 1997, "Yeast microarrays for genome wide parallel genetic and gene expression analysis", Proc Natl Acad Sci USA 94:13057–13062.
Lockhart et al., 1996, "Expression monitoring by hybridization to high–density oligonucleotide arrays", Nat Biotechnol 14:1675–1680.
Marshall and Hodgson, 1998, "DNA chips: an array of possibilities", Nat Biotechnol 16:27–31.
Maskos and Southern, 1992, "Oligonucleotide hybridizations on glass supports: a novel linker for oligonucleotide synthesis and hybridization properties of oligonucleotides synthesised in situ", Nucleic Acids Res 20:1679–1684.
Nguyen et al., 1995, "Differential gene expression in the murine thymus assayed by quantitative hybridization of arrayed cDNA clones", Genomics 29:207–216.
Pease et al., 1994, "Light–generated oligonucleotide arrays for rapid DNA sequence analysis", Proc Natl Acad Sci USA 91:5022–5026.
Ramsey, 1998, "DNA chips: state–of–the art", Nat Biotechnol 16:40–44.
Schena et al., 1995, "Quantitative monitoring of gene expression patterns with a complementary DNA microarray", Science 270:467–470.
Schena et al., 1996, "Parallel human genome analysis: microarray–based expression monitoring of 1000 genes", Proc Natl Acad Sci USA 93:10614–10619.
Shalon et al., 1996, "A DNA microarray system for analyzing complex DNA samples using two–color fluorescent probe hybridization", Genome Res 6:639–645.
Stollar and Rashtchian, 1987, "Immunochemical approaches to gene probe assays", Anal Biochem 161:387–394.
Wodicka et al., 1997, "Genome–wide expression monitoring in *Saccharomyces cerevisiae*", Nat Biotechnol 15:1359–1367.

* cited by examiner

Primary Examiner—Eggerton A. Campbell
(74) Attorney, Agent, or Firm—Pennie & Edmonds LLP (57) ABSTRACT

The present invention relates to anti-heteronucleic acid antibodies and their uses for detection of RNA-DNA duplexes on arrays. The invention provides a method for detection of total cellular RNA hybridization on microarrays, thus obviating the need for isolation of the poly(A)$^+$ fraction.

98 Claims, 3 Drawing Sheets

MONITORING OF GENE EXPRESSION BY DETECTING HYBRIDIZATION TO NUCLEIC ACID ARRAYS USING ANTI-HETERONUCLEIC ACID ANTIBODIES

1. FIELD OF THE INVENTION

The present invention relates to methods and compositions for detecting, monitoring and/or quantifying gene expression using nucleic acid arrays, in particular, by using anti-heteronucleic acid antibodies to detect RNA-DNA duplexes on microarrays.

2. BACKGROUND

Modern biology teaches the importance of genes and gene expression to processes of health and disease. New individual genes causing or predisposing to conditions or diseases are now reported almost daily. Additionally, it is commonly understood that observing and measuring patterns of gene expression in health and disease will contribute immensely to further understanding of these states. Therefore, any observational method that can rapidly, accurately, and economically observe and measure the presence or expression of selected individual genes or of whole genomes will be of great value. Of even more value will be methods that can directly and quantitatively be applied to RNA typically derived directly from biological samples.

2.1 Methods for Monitoring Gene Expression

Current observation and measurement methods suffer from one or more disadvantages that render them unnecessarily inaccurate, time consuming, labor intensive, or expensive. Such disadvantages flow from requirements for, e.g., prior knowledge of gene sequences, cloning of complex mixtures of sequences into many individual samples each of a single sequence, repetitive sequencing of sample nucleic acids, electrophoretic separations of nucleic acid fragments, and so forth.

For example, observation techniques for individual mRNA or cDNA molecules, such as Northern blot analysis, RNase protection, or selective hybridization to arrayed cDNA libraries (see Sambrook et al., *Molecular Cloning—A Laboratory Manual*, Cold Spring Harbor Press, New York (1989)) depend on specific hybridization of a single oligonucleotide probe complementary to the known sequence of an individual molecule. Since a single human cell is estimated to express 10,000–30,000 genes (Liang et al., 1992, Science, 257:967–971), most of which remain unknown, single probe methods to identify all sequences in a complex sample are prohibitively cumbersome and time consuming.

Similarly, traditional nucleic acid sequencing (Sanger et al., 1977, Proc. Natl. Acad. Sci. USA, 74:5463–5467), sequencing by hybridization ("SBH") using combinatorial probe libraries (Drmanac et al., 1993, Science 260:1649–1652; U.S. Pat. No. 5,202,231, Apr. 13, 1993 to Drmanac et al.), or classification by oligomer sequence signatures (Lennon et al., 1991, Trends Genetics 7:314–317), and positional SBH (Broude et al., 1994, Proc. Natl. Acad. Sci. USA 91:3072–3076) also require that samples be arrayed into purified clones, making the methods inappropriate for complex mixtures.

Several approaches have been described that attempt to characterize complex mixtures of nucleic acids without cloning, all of which at least require electrophoretic separation and/or traditional sequencing. A basic approach is that of differential display (Liang et al., 1992, Science 257:967–71; Liang et al., 1995, Curr. Op. Immunol. 7:274–280), which uses the polymerase chain reaction ("PCR") with an oligo (dT) primer and a degenerate primer designed to hybridize within a few hundred bases of the cDNA 3'-end. The resulting DNA subsequences of varying length are electrophoretically separated to yield a pattern of, preferably, 100–250 bands. This approach, at best providing only qualitative "fingerprints" of gene expression, suffers from well-known problems, including a high false positive rate, migration of multiple nucleic acid species within a single observed band, and non-quantitative results. Further, putative gene identification depends on purification and traditional sequencing of the components in electrophoretic bands.

Additionally, approaches have been described which attempt to improve differential display, but without obviating the need for traditional sequencing and/or electrophoretic separation. For example, a method described in European Patent Application 0 534 858 A1 (published Mar. 31, 1993), is directed to applying differential display to gDNA samples by using restriction endonuclease ("RE") digestion together with PCR employing phasing primers in order to reduce the complexity of such samples to levels electrophoretically observable. The multiple phasing primers divide the gDNA samples in multiple pools of lower complexity, which are electrophoretically separated to yield qualitative "fingerprints."

Other methods improving on differential display include the following, all of which are similarly limited to generating electrophoretic "fingerprints." One such improvement is described in U.S. Pat. No. 5,459,937 (Oct. 17, 1995). This method generates multiple pools of lower complexity by using sequential rounds of PCR applied to 3'-end fragments of cDNAs. The 3'-end fragments lie between a recognition site for a frequently-cutting RE and the poly(A) tail of the cDNA. Fragments in the multiple pools are finally putatively identified by electrophoretic separation and individual sequencing. Another example of such an improvement is described by Prashar et al., 1996, Proc. Natl. Acad. Sci. USA 93:659–663. Primarily, this reference describes an alternative method for generating similar 3'-end fragments, which lie between a recognition site for a frequently-cutting RE and the poly(A) tail of the cDNA.

Differing from differential display is another class of methods, which observe gene expression by sampling, that is, these methods repetitively sequence nucleic acids in a sample and count the sequence occurrences in order to statistically observe gene expression. Such methods require sequencing and are statistically limited in their ability to discover rare transcripts. An early example of such a method determined and counted expressed sequence tags ("ESTs"), and is described in Adams et al., 1991, Science, 252:1651–1656. Another example is named "serial analysis of gene expression" (Velculescu et al., 1995, Science, 270:484–487). According to this method, cDNA molecules are converted into representative "tags," which are short oligonucleotides generated from Type IIS RE single-stranded overhangs located at determined distances from the 3'-end of source cDNA. (Type IIS REs cleave a defined distance (up to 20 bp) away from their asymmetric recognition sites (Szybalski, 1985, Gene 40:169). Approximate, putative identification of the source of a tag requires sequencing the tag and using the sequence and location information to look up possible source sequences in a nucleic acid sequence database.

Other methods for gene and gene-expression measurement, although unrelated to differential display, still, e.g., require electrophoretic separation. Such a method is described in PCT Publication WO 97/15690. According to this method "signals" are generated that represent the length of a nucleotide sequence between defined subsequences in a target nucleic acid. The defined subsequences are preferably restriction endonuclease sites or oligomer binding sites. These signals can then be compared to results of computer simulated signal generation experiments using computer databases of nucleic acid sequences. By this comparison, particular DNA sequences in the database can be identified as present in a sample, since they are predicted to generate signals which are also observed. The length information of the signals of this method is observed electrophoretically.

Many of the methods previously described for the analysis of complex mixtures of nucleic acids require electrophoretic separation, possibly together with nucleic acid cloning and sequencing. These procedures can be unnecessarily labor intensive, slow, and uneconomical. Recently new approaches have been reported that can, in some implementations, obviate the need for, at least, electrophoretic separation. Such methods depend on hybridization of probe oligonucleotides to recognize short subsequences of from 4 to 20 base pairs on target nucleic acids. The oligonucleotides can be either present in solution or arrayed on a planar surface, such as a glass chip ("chip").

Subsequence recognition by hybridization performed in solution, however, often requires electrophoretic separation. Methods reported in Smith (Smith, 1992, PCR Methods and Applications 2:21–27) and in Unrau et al. (Unrau et al., 1994, Gene 145:163–169) use type IIS or interrupted palindromic ("IP") REs to create single-stranded overhangs of unknown sequence from a sample of cDNAs. These overhangs are recognized by hybridization to a plurality of degenerate adapters (called "indexers" in the latter reference), each possible overhang being recognizable by the one adapter having a complementary single-stranded terminus. The adapters also include primer sequences, and successful hybridization of an adapter is detected by electrophoretic separation of PCR amplification products.

Hybridization specificity can be improved by using a ligase, which requires exact base-pairing for ligation. See, e.g., Landegren et al., 1988, Science, 241, 1077–1080, in which hybridization is only recognized if two probe oligonucleotides hybridize to adjacent position on a target DNA sequence and are ligated by T4 DNA ligase. "Strandinvasion" (Guilfoyle et al., 1997, Nucleic Acids Res. 25:1854–1858) is an extension of the indexing approach designed to further improve hybridization specificity. In strand-invasion, the duplex adapter, or indexer, has a longer single-stranded terminus which has a few determined nucleotides terminal to the previously described degenerate subsequence. The extra, determined nucleotides "invade" into and base pair with a known terminal subsequence of the RE recognition sites, which is adjacent to the unknown single-stranded overhangs that the indexers recognize, thereby improving hybridization stringency. Again, successfully hybridized adapters are recognized by PCR amplification and electrophoretic separation.

Electrophoretic separations can be obviated by arraying the probe oligonucleotides on a chip. DNA arrays, consisting of thousands of DNA sequences printed at high density on a solid support, can be used for large-scale gene expression analysis (Ramsey, 1998, Nat. Biotechnol. 16:40–44; Marshall and Hodgson, 1998, Nat. Biotechnol. 16:27–31). Chips can be prepared by depositing already synthesized probe oligonucleotides on a derivatized glass surface, or by synthesizing the probe oligonucleotides directly on the glass surface using a combination of photolithography and oligonucleotide chemistry (Lashkari et al., 1997, Proc. Nat. Acad. Sci. USA 94:13057–13062; DeRisi et al., 1997, Science, 278:680–686; Wodicka et al., 1997, Nat. Biotechnol. 15:1359–1367; Chee et al., 1996, Science 274:610–614). These probe oligonucleotides are typically designed to hybridize to 10, 15, or 20 bases of a target DNA. Chips capable of recognizing in principle up to 6500 genes have been prepared. The chips are hybridized to samples of fluorescently tagged target DNAs, and are then imaged to determine to which oligonucleotides hybridization has occurred. Total cDNA or mRNA samples can be used with this procedure, so that expression of thousands of genes in complex mixtures of cellular mRNA species can be simultaneously monitored (DeRisi et al., 1997, Science 278:680–686). This permits the detection within a defined cell population of characteristic transcript "signature" patterns which may be perturbed in characteristic ways by genetic mutations (DeRisi et al., supra), or manipulations of experimental conditions (DeRisi et al., supra; Wodicka, L., et al., 1997, Nat. Biotechnol. 15:1359–1367). The latter finding suggests that DNA microarrays may be useful for distinguishing desirable or undesirable effects during drug screening.

Although some success has been reported with such chips, well-known problems remain, including those of obtaining unambiguous and reliable hybridization signals. Typically, techniques to prepare labeled DNAs require isolation of the poly(A)$^+$ fraction of total cellular RNA, transcription of mRNA by oligo dT-primed or random-primed reverse transcription, and labeling of cDNA by enzymatic or chemical methods. A large number of cells are necessary to produce the required amounts of mRNA. In addition, such labeling may alter the ability of the labeled polynucleotide to hybridize to the complementary sequence. Thus, existing techniques to prepare labeled samples are tedious, time-consuming and relatively insensitive. Current methods for solving such signal to noise problems call for the use of significantly redundant sets of probe oligonucleotides. For example, to observe one subsequence of one gene currently requires the synthesis of multiple (greater than 20 per gene) overlapping and mismatched oligonucleotide probes in order to obtain statistically significant data, including data necessary to apply corrections for mismatched hybridizations or nonspecific binding. The need for such redundancy of immobilized probes poses serious throughput and cost limitations, especially in view of the 130,000 or so genes possibly expressed in human tissues.

Various hybridization alternatives include the use of arrays of peptide nucleic acids ("PNA") (Weiler et al., Nucleic Acids Res. 25, 2792–2799 (1997)). PNAS, having the bases linked via N-(2-aminomethyl)-glycine moiety, obey Watson-Crick base-pairing rules with DNA but with greater stability than corresponding DNA:DNA hybrids. In another alternative, PCR amplified target DNAs, prepared perhaps from ESTs or cDNA libraries, are physically tethered onto a planar surface instead of arrays of probe oligonucleotides.

The observational methods for gene expression described above are not capable of rapidly, accurately, and economically observing and measuring the presence or expression of selected individual genes or of whole genomes. These methods typically require, for example, prior knowledge of gene sequences, or cloning of complex mixtures of sequences into many individual samples of a single sequence, or repetitive sequencing of sample components, or electrophoretic separations, and so forth. Importantly, they have not been able to accurately and economically utilize the potential of arrayed nucleic acids.

Accordingly, a method that overcomes these disadvantages will be of great value.

2.2 Anti-heteronucleic Antibodies

Antibodies that can distinguish the various helical shapes (A, B, and Z) of nucleic acids are reviewed in Fliss et al., 1993, Appl. Environ. Microbiol. 59:2698–705. In particular, animals immunized with nucleic acids in the helical A conformation (RNA-DNA or RNA-RNA hybrids) produce antibodies which are backbone specific and show little dependence upon base specificity (Stollar et al., 1987, Anal. Biochem. 161:387–94). Anti-RNA-DNA antibodies do not recognize double stranded DNA because of the different conformation of its helix (B conformation). A monoclonal antibody which specifically binds DNA-RNA hybrids has been described for use in solution in nucleic acid hybridization assay mixtures (Carrico, U.S. Pat. No. 4,833,084, May 23, 1989). Stuart et al., U.S. Pat. No. 4,732,847, Mar. 22, 1988 describes a method for detecting the presence of a DNA or RNA sequence hybridized to the other type of nucleic acid sequence fixed to a solid support using mouse monoclonal antibodies which bind DNA-RNA hybrid complexes. Assays based on detecting DNA-RNA hybrids formed in solution using anti-heteronucleic acid ("anti-HNA") monoclonal antibodies immobilized on a microtiter plate have been used for the detection of microorganism transcripts (Coutlée et al., 1991, Anal. Biochem. 181:96–105; DIGENE, Beltsville, Md.).

Citation of a reference herein shall not be construed as an admission that such is prior art to the present invention.

3. SUMMARY OF THE INVENTION

The present invention relates to compositions and methods for detecting, measuring or monitoring gene expression by detecting hybridization of RNA or RNA mimics (collectively referred to often herein as "target RNA") to DNA arrays. Techniques relied on in the prior art to detect hybridization on nucleic acid arrays typically require isolation of the poly(A)$^+$ fraction of total cellular RNA for preparation of labeled target, as well as RNA or cDNA labeled reactions. These techniques are tedious, time consuming, and relatively insensitive. In contrast, the present invention provides a sensitive, specific method for detecting or measuring hybridization on nucleic acid arrays using anti-heteronucleic acid ("anti-HNA") antibodies to detect RNA-DNA duplexes on arrays, preferably, to detect RNA hybridization on DNA microarrays using RNA probes derived directly from the cell or which have not been subjected to reverse transcription, e.g., total cellular RNA.

This invention provides methods for simultaneously monitoring, detecting and/or quantifying the expression of a multiplicity of genes. The levels of transcription for virtually any number of genes may be determined simultaneously. Typically, at least about 10 genes, preferably at least about 100, more preferably at least about 1000 and most preferably at least about 10,000 different genes are assayed at one time.

The methods involve providing a pool of target nucleic acids including but not limited to, total cellular RNA, poly(A)$^+$ messenger RNA ("mRNA"), fractions thereof or RNA transcribed from cDNA; hybridizing the pool of nucleic acids to an array of probe DNA or DNA mimics immobilized on a surface of a solid phase to form heteroduplexes; and contacting anti-HNA antibodies with the heteroduplexes under conditions such that immunospecific binding between the antibody and the heteroduplexes can occur. The probe DNA or DNA mimics are nucleic acids that comprise at least a hybridizable sequence of DNA or DNA mimics.

In one embodiment, this invention provides a method for detecting or measuring the amount of target RNA hybridized to an array of probe DNA or DNA mimics immobilized on a surface of a solid phase comprising: (a) contacting said array containing or suspected of containing target RNA hybridized thereto, with an antibody, said antibody being immunospecific to RNA-DNA duplexes, under conditions such that immunospecific binding between said antibody and any RNA-DNA duplexes on said surface can occur; and (b) detecting or quantifying any binding of said antibody to said duplexes on said surface, wherein the presence or amount of antibody so bound indicates the presence or amount, respectively, of target RNA bound to probe DNA or DNA mimics on said surface.

In another embodiment, this invention provides a method for detecting or measuring the amount of target RNA hybridized to an array of probe DNA or DNA mimics immobilized on a surface of a solid phase comprising: (a) contacting said target RNA with said probe DNA or DNA mimics on said array under conditions such that hybridization to form RNA-DNA duplexes can occur; (b) contacting the surface of said array, with an antibody, said antibody being immunospecific to RNA-DNA duplexes, under conditions such that immunospecific binding between said antibody and any RNA-DNA duplexes on said surface can occur; and (c) detecting or quantifying any binding of said antibody to said duplexes on said surface, wherein the presence or amount of antibody so bound indicates the presence or amount, respectively, of target RNA bound to probe DNA or DNA mimics on said surface.

In another embodiment, this invention provides a nucleic acid array comprising target RNA hybridized to one or more probe DNA or DNA mimics within an array of probe DNA or DNA mimics immobilized on a surface of a solid phase to form RNA-DNA duplexes, further comprising an antibody immunospecifically bound to said RNA-DNA duplexes, said antibody being immunospecific to RNA-DNA duplexes.

In another embodiment, this invention provides a method of expression analysis of a cell comprising: (a) contacting a population of RNA isolated from said cell with an array of probe DNA or DNA mimics, wherein the probe DNA or DNA mimics is immobilized on a surface of a solid phase under conditions such that hybridization to form DNA-RNA duplexes can occur; (b) contacting the surface of said array with an antibody, said antibody being immunospecific to RNA-DNA duplexes, under conditions such that immunospecific binding between said antibody and any RNA-DNA duplexes on said surface can occur; and (c) detecting or quantifying any binding of said antibody to said duplexes on said surface, wherein the presence or amount of antibody so bound indicates the presence or amount, respectively, of target RNA bound to probe DNA or DNA mimics on said surface.

In an embodiment, the probe DNA or DNA mimics is a plurality of DNA species each of known different sequences, each species being situated at a known location on the surface of the solid phase.

In an embodiment, the DNA species are polynucleotides.

In another embodiment, the DNA species are oligonucleotides, preferably of less than 50 bases in length. In another embodiment the DNA species are cDNA.

In an embodiment, the target RNA is total cellular RNA from one or more cells. In another embodiment, the target RNA is a plurality of distinct RNA species. In an embodiment, the individual RNA species are less than 0.01% of the target RNA (i.e., less than 1 part in 10,000).

The anti-HNA antibodies may be labeled before, during, or after contacting the array although in a preferred embodiment, the antibodies are labeled before contacting the array. Fluorescence labels are preferred. In a preferred embodiment, the anti-HNA antibodies are monoclonal antibodies.

The method can additionally include a step of quantifying the level of abundances of target RNA by measuring the amount of bound anti-HNA antibody, and thereby measuring the amount of RNA hybridized to a particular complementary DNA or DNA mimic on the array. In another embodiment, the method can additionally include a step of quantifying the level of abundances of individual RNA species within a plurality of distinct RNA species. In a preferred embodiment, the pool of target nucleic acids is one in which the concentration of the target nucleic acids is proportional to the expression levels of genes encoding those target nucleic acids.

In a preferred embodiment, the microarray is a high density array, comprising greater than about 100, preferably greater than about 1,000, more preferably greater than about 3,000, most preferably greater than about 5,000 different nucleic acid probes. Such high density probes comprise a probe density of greater than about 50, preferably greater than about 500, more preferably greater than about 1,000, most preferably greater than about 2,000 different nucleic acid probes per cm². Although a planar array surface is preferred, the array may be fabricated on a surface of virtually any shape or even a multiplicity of surfaces. The array may further comprise mismatch control probes.

Arrays for the practice of this invention can be synthesized by several methods including but not limited to chemical synthesis by parallel immobilized polymer synthesis methods or light directed polymer synthesis methods.

The array includes detection DNA or DNA mimic probes which are probes each of which has a sequence that is complementary to at least a subsequence of the RNA whose expression is desired to be detected. In addition, the array can contain normalization controls, mismatch controls and expression level controls as described herein.

In a specific embodiment, hybridization is at low stringency with at least one wash at higher stringency. Hybridization may include subsequent washes at progressively increasing stringency until a desired level of hybridization specificity is reached.

Quantification of the bound antibody can be by any means known to one of skill in the art. In a specific embodiment in which the antibody is fluorescently labeled, quantification is achieved by use of a confocal fluorescence microscope. Data are preferably evaluated by calculating the difference in signal intensity between each DNA probe and its corresponding mismatch control probe. It is particularly preferred that this difference be calculated and evaluated for each gene.

In an embodiment of the invention, expression of genes involved in the pathways associated with various pathological conditions (e.g. cancer) and whose expression is thus indicative of the pathological condition are monitored.

In another embodiment, this invention provides a method of identifying genes that are effected by one or more drugs, or conversely, screening a number of drugs to identify those that have an effect on particular gene(s).

In another embodiment, the methods of the invention include observing differential gene expression between pairs of tissues in defined biological states.

This invention also provides kits comprising nucleic acid arrays and anti-heteronucleic acid antibodies.

As will be apparent to the skilled artisan, the methods of the invention are also applicable to the situation where anti-HNA antibodies are used to detect RNA-DNA duplexes generated by hybridizing target DNA (or DNA mimics) to an array containing RNA (or RNA mimics) immobilized on the surface of a solid phase. Accordingly, in a specific embodiment, this invention provides a method for detecting or measuring the amount of target DNA hybridized to an array of probe RNA immobilized on a surface of a solid phase comprising: (a) contacting said array containing or suspected of containing target DNA hybridized thereto, with an antibody, said antibody being immunospecific to RNA-DNA duplexes, under conditions such that immunospecific binding between said antibody and any RNA-DNA duplexes on said surface can occur; and (b) detecting or quantifying any binding of said antibody to said duplexes on said surface, wherein the presence or amount of antibody so bound indicates the presence or amount, respectively, of target DNA bound to probe RNA on said surface.

In another embodiment, this invention provides a method for detecting or measuring the amount of target DNA hybridized to an array of probe RNA immobilized on a surface of a solid phase comprising: (a) contacting said target DNA with said probe RNA on said array under conditions such that hybridization to form RNA-DNA duplexes can occur; (b) contacting the surface of said array, with an antibody, said antibody being immunospecific to RNA-DNA duplexes, under conditions such that immunospecific binding between said antibody and any RNA-DNA duplexes on said surface can occur; and (c) detecting or quantifying any binding of said antibody to said duplexes on said surface, wherein the presence or amount of antibody so bound indicates the presence or amount, respectively, of target DNA bound to probe RNA on said surface.

In another embodiment, this invention provides a nucleic acid array comprising target DNA hybridized to one or more probe RNA within an array of probe RNA immobilized on a surface of a solid phase to form RNA-DNA duplexes, further comprising an antibody immunospecifically bound to said RNA-DNA duplexes, said antibody being immunospecific to RNA-DNA duplexes.

This Summary is not limiting. Other embodiments and applications will be apparent to one of average skill in view of the following figures and description.

4. BRIEF DESCRIPTION OF THE FIGURES

FIGS. 2A, 2C, and 2E) or 60° C. (FIGS. 2B, 2D, and 2F). Hybridization in FIGS. 2C–2F was detected with an AP-conjugated anti-HNA mAb and ELF-97 substrate, as in FIG. 1. Shown are histograms depicting the distribution of fluorescent intensities for individual genes distributed on the half genome array.

5. DETAILED DESCRIPTION

The instant invention relates to methods and compositions for monitoring, detecting and/or quantifying the expression levels of one or more genes. These methods are based on novel uses of anti-HNA antibodies for binding to RNA hybridized to DNA arrays, containing a population of DNA preferably attached to a planar surface, such as a glass chip. In an alternative embodiment, this invention provides methods based on novel uses of anti-ENA antibodies for binding to DNA hybridized to RNA arrays, containing a population of RNA preferably attached to a planar surface, such as a glass chip.

In the following, the methods for detection of gene expression are first generally described in Section 5.1 followed in Section 5.2 by a description of the applications of the method of the instant invention.

The practice of the present invention employs, unless otherwise indicated, conventional techniques of cell biology, cell culture, molecular biology, microbiology, recombinant DNA, immunology, transgenic animal technology, and pharmacology. See, e.g., Sambrook et al., *Molecular Cloning A Laboratory Manual*, Cold Spring Harbor Press, (2nd. ed., 1989); Glover ed., *DNA Cloning*, Vol 1 and 2 (1985); Gait ed., *Oligonucleotide Synthesis* (1984); Hames et al. eds., *Transcription and Translation* (1984); Freshney, *Culture of Animal Cells*, Alan N. Liss, Inc. (1997); *Immobilized Cells and Enzymes*, IRL Press (1986); Perbal, *A Practical Guide to Molecular Cloning, Methods in Enzymology*, Academic Press (1984); Miller et al. eds., *Gene Transfer Vectors for Mammalian Cells*, Cold Spring Harbor Laboratory (1987); Wu et al. eds., *Methods in Enzymology*, Vols 154 and 155; Mayer et al. eds., *Immunochemical Methods in Cell and Molecular Biology*, Academic Press (1987); Weir et al. eds., *Handbook of Experimental Immunology*, Vols 1–4 (1986).

5.1 Measurement of Gene Expression Levels

Preferably, measurement of gene expression is made by hybridization of RNA to microarrays consisting of a solid phase on the surface of which is immobilized a population of DNA or DNA mimics, which are described in the next subsection. Alternatively, the microarrays for use in the present invention consist of a solid phase on the surface of which is immobilized a population of RNA, to which DNA or DNA mimics are then hybridized.

5.1.1 Microarrays Generally

In a preferred embodiment the present invention makes use of "microarrays". A microarray is generally an array of less than 6.25 cm$^2$ in size (although the contiguous solid phase can be much larger). Generally, a microarray is about 1.6 cm$^2$ to 6.25 cm$^2$ in size. Microarrays can be employed for analyzing the transcriptional state in a cell, e.g., for measuring the transcriptional states of cells exposed to graded levels of a drug of interest or to graded perturbations to a biological pathway of interest.

A microarray for use in the present invention is a solid phase surface with an ordered array of nucleic acids that provide hybridization sites for products of many of the genes in the genome of a cell or organism, preferably most or almost all of the genes. Microarrays can be made in a number of ways, of which several are described below. However produced, microarrays share certain characteristics: The arrays are reproducible, allowing multiple copies of a given array to be produced and easily compared with each other. Preferably the microarrays are small, usually smaller than 5 cm$^2$, and they are made from materials that are stable under binding (e.g. nucleic acid hybridization) conditions. A given binding site or unique set of binding sites in the microarray will preferably specifically bind the product of a single gene in the cell. Although there may be more than one physical binding site (hereinafter "site") per specific RNA or DNA, for the sake of clarity the discussion below will assume that there is a single site.

The array includes test probes which are nucleic acid probes each of which has a sequence that is complementary to a subsequence of the RNA whose expression is to be detected.

In an embodiment wherein the array includes detection RNA or RNA mimic probes, the array further includes test probes which are probes each of which has a sequence that is complementary to at least a subsequence of the DNA desired to be detected.

In addition, the array can contain normalization controls, mismatch controls and expression level controls.

In preferred embodiments, RNAs from two different cells are monitored. In the case of drug responses RNA from one cell exposed to a drug is compared to RNA from a cell of the same type not exposed to the drug. In the case of pathway responses RNA from one cell exposed to a pathway perturbation is compared to RNA from another cell of the same type not exposed to the pathway perturbation. In the case of disease states, e.g., cancer, RNA from a cancer cell is compared to RNA from a normal cell.

5.1.2 Preparation of Microarrays

Microarrays for use in the present invention are known in the art and consist of a surface to which probes (DNA or DNA mimics) that correspond in sequence (i.e. comprise the inverse complement and can therefore hybridize) to RNA, can be specifically hybridized or bound, preferably at a known position. In an alternative embodiment, microarrays for use in the present invention consist of a surface to which probe RNA that corresponds in sequence (i.e. comprise the inverse complement and can therefore hybridize) to DNA, can be specifically hybridized or bound, preferably at a known position. Each probe preferably has a different nucleic acid sequence. The position of each probe on the solid surface is preferably known. In one embodiment, the microarray is a high density array, preferably having a density of greater than about 60 different probes per 1 cm$^2$. In one embodiment, the microarray is an array (i.e., a matrix) in which each position represents a discrete binding site for a product encoded by a gene (i.e., RNA), and in which binding sites are present for products of most or almost all of the genes in the organism's genome. In a preferred embodiment, the "binding site" (hereinafter, "site") is a DNA or DNA analogue (mimic) to which a particular RNA can specifically hybridize. The DNA or DNA mimic of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A gene is identified as an open reading frame (ORF) of preferably at least 50, 75, or 99 amino acids from which a messenger RNA is transcribed in the organism (e.g., if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the *Saccharomyces cerevisiae* genome has been completely sequenced and is reported to have approximately 6275 open reading frames (ORFS) longer than 99 amino acids. Analysis of these ORFs indicates that there are 5885 ORFs that are likely to specify protein products (Goffeau et al., 1996, *Science* 274:546–4567). In contrast, the human genome is estimated to contain approximately $10^5$ genes.

5.1.3 Preparing Probes for Microarrays

As noted above, the "binding site" to which a particular RNA specifically hybridizes according to the invention is a complementary DNA or DNA mimic attached at that binding site. In one embodiment, the binding sites of the microarray are DNA or DNA mimics (including derivatives and analogues) corresponding to at least a portion of each gene in an organism's genome. In another embodiment, the binding site of the microarray to which a particular DNA specifically hybridizes according to the invention is a complementary RNA.

DNA mimics are polymers composed of subunits capable of specific, Watson-Crick-like hybridization with DNA or specific hybridization with RNA. The nucleic acids can be modified at the base moiety, sugar moiety, or phosphate backbone.

DNA can be obtained by, e.g., polymerase chain reaction (PCR) amplification of gene segments from genomic DNA, cDNA (e.g., by RT-PCR), or cloned sequences. PCR primers are preferably chosen based on the known sequence of the genes or cDNA, that result in amplification of unique fragments (i.e. fragments that do not share more than 10 bases of contiguous identical sequence with any other fragment on the microarray). Computer programs are useful in the design of primers with the required specificity and optimal amplification properties. See, e.g., Oligo version 5.0 (National Biosciences). Typically each probe on the microarray will be between about 20 bases and about 2000 bases, more typically between about 100 bases and about 1000 bases, and usually between about 300 bases and about 800 bases in length. PCR methods are well known and are described, for example, in Innis et al. eds., 1990, *PCR Protocols: A Guide to Methods and Applications*, Academic Press Inc. San Diego, Calif. It will be apparent that computer controlled robotic systems are useful for isolating and amplifying nucleic acids.

An alternative means for generating the nucleic acids for the microarray is by synthesis of synthetic polynucleotides or oligonucleotides, e.g., using N-phosphonate or phosphoramidite chemistries (Froehler et al., 1986, *Nucleic Acid Res* 14:5399–5407; McBride et al., 1983, *Tetrahedron Lett.* 24:245–248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, *Nature* 365:566–568; see also U.S. Pat. No. 5,539,083).

In an alternative embodiment, the hybridization sites are made from plasmid or phage clones of genes, cDNAs (e.g., expressed sequence tags), or inserts therefrom (Nguyen et al., 1995, *Genomics* 29:207–209).

5.1.4 Attaching Probes to the Solid Surface

The probes are attached to a solid support, which may be made from glass, plastic (e.g., polypropylene, nylon), polyacrylamide, nitrocellulose, or other materials, and may be porous or nonporous. A preferred method for attaching the nucleic acids to a surface is by printing on glass plates, as is described generally by Schena et al., 1995, *Science* 270:467–470. This method is especially useful for preparing microarrays of cDNA. See also DeRisi et al., 1996, *Nature Genetics* 14:457–460; Shalon et al., 1996, *Genome Res.* 6:639–645; and Schena et al., 1995, *Proc. Natl. Acad. Sci. USA* 93:10539–11286. Blanchard discloses the use of an ink jet printer for oligonucleotide synthesis (U.S. application Ser. No. 09/008,120, filed Jan. 16, 1998, which is incorporated by reference herein in its entirety for all purposes).

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, *Science* 251:767–773; Pease et al., 1994, Light-directed oligonucleotide arrays for rapid DNA sequence analysis, *Proc. Natl. Acad. Sci. USA* 91:5022–5026; Lockhart et al., 1996, Expression monitoring by hybridization to high-density oligonucleotide arrays, *Nature Biotech* 14:1675; U.S. Pat. Nos. 5,578,832; 5,556,752; and 5,510,270, each of which is incorporated by reference herein in its entirety for all purposes) or other methods for rapid synthesis and deposition of defined oligonucleotides (Blanchard et al., 1996, High-Density Oligonucleotide arrays, *Biosensors & Bioelectronics* 11: 687–90). When these methods are used, oligonucleotides (e.g., 20-mers) of known sequence are synthesized directly on a surface such as a derivatized glass slide. Usually, the array produced is redundant, with several oligonucleotide molecules per RNA. Oligonucleotide probes can be chosen to detect alternatively spliced mRNAs.

Other methods for making microarrays, e.g., by masking (Maskos and Southern, 1992, *Nuc. Acids Res.* 20:1679–1684), may also be used. In principal, any type of array, for example, dot blots on a nylon hybridization membrane (see Sambrook et al., Molecular Cloning—A Laboratory Manual (2nd Ed.), Vol. 1–3, Cold Spring Harbor Laboratory, Cold Spring Harbor, N.Y., 1989, which is incorporated in its entirety for all purposes), could be used, although, as will be recognized by those of skill in the art, very small arrays will be preferred because hybridization volumes will be smaller. Presynthesized probes can be attached to solid phases by methods known in the art (see e.g., Section 6.1).

5.1.5 Target Nucleic Acids

The target nucleic acids are comprised of RNA or mimics (derivatives, analogues) thereof. In a preferred embodiment, the targets comprise RNA including but not limited to, total cellular RNA, poly(A)$^+$ messenger RNA ("mRNA"), fractions thereof or RNA transcribed from cDNA. Methods for preparing total and poly(A)$^+$ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, Biochemistry 18:5294–5299). Poly(A)$^+$ RNA is selected by selection with oligo-dT cellulose (see Sambrook et al., supra). Cells of interest include but are not limited to wild-type cells, drug-exposed wild-type cells, modified cells, diseased cells, and in particular, cancer cells.

In one embodiment, RNA can be fragmented by methods known in the art, e.g., by incubation with $ZnCl_2$, to generate fragments of RNA for use as target RNA.

In one embodiment, isolated mRNA can be converted to antisense RNA synthesized by in vitro transcription of double-stranded cDNA in the presence of labeled dNTPs (Lockhart et al., 1996, Nature Biotech. 14:1675).

5.1.6 Hybridiztion to Microarrays

Nucleic acid hybridization and wash conditions are chosen so that the target RNA "specifically binds" or "specifically hybridizes" to its complementary DNA of the array, preferably to a specific array site, wherein its complementary DNA is located, i.e., the RNA hybridizes, duplexes or binds to a sequence array site with a complementary DNA probe sequence but does not substantially hybridize to a site with a non-complementary DNA sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Arrays containing double-stranded probe DNA situated thereon are preferably subjected to denaturing conditions to render the DNA single-stranded prior to contacting with the target RNA. Arrays containing single-stranded probe DNA (e.g., synthetic oligodeoxyribonucleic acids) need not be denatured prior to contacting with the target RNA.

Optimal hybridization conditions will depend on the length (e.g., oligomer versus polynucleotide greater than 200 bases) and type (e.g., RNA, DNA) of probe and target nucleic acids. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York. When the cDNA microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93:10614). Useful hybridization conditions are also provided in, e.g., Tijessen, 1993, Hybridization With Nucleic Acid Probes, Elsevier Science Publishers B.V. and Kricka, 1992, Nonisotopic DNA Probe Techniques, Academic Press San Diego, Calif.

5.1.7 Obtaining Anti-HNA Antibodies

Anti-HNA antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Preferably the anti-HNA antibody is a monoclonal antibody of high specificity and avidity.

In specific embodiments, anti-HNA antibodies that can be used in the present invention include, but are not limited to, those described in Fliss et al., 1993, App. Environ. Microb. 59(8):2698–2705; Stollar et al., 1987, Anal. Biochem. 161:387–394; Carrico, U.S. Pat. No. 4,833,084, May 23, 1989; Coutlée et al., 1989, Anal. Biochem. 181:96–105.

Various procedures known in the art may be used for the production of polyclonal antibodies which specifically bind RNA-DNA duplexes. For the production of polyclonal antibody, various host animals can be immunized by injection with the RNA-DNA duplexes, including but not limited to rabbits, mice, rats, chickens, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and corynebacterium parvum.

For preparation of monoclonal antibodies directed toward a RNA-DNA duplexes, any technique which provides for the production of antibody molecules by continuous cell lines in culture may be used. For example, the hybridoma technique originally developed by Kohler and Milstein (1975, Nature 256, 495–497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77–96).

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entireties.)

In addition, techniques have been developed for the production of humanized antibodies. (See, e.g., Queen, U.S. Pat. No. 5,585,089 and Winter, U.S. Pat. No. 5,225,539, which are incorporated herein by reference in their entirety.) An immunoglobulin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against a RNA-DNA duplexes. Single chain antibodies are formed by linking the heavy and light chain fragments of the Fv region via an amino acid bridge, resulting in a single chain polypeptide.

Antibody fragments that recognize specific epitopes (i.e., that contain the binding region of the antibody) may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

5.1.8 Labeling Anti-HNA Antibodies

Described herein are methods for detectably labeling antibodies capable of specifically binding RNA-DNA duplexes. The labeling methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. Any labels known in the art may be used, including but not limited to radiolabels such as $^{14}C$, $^{3}H$, $^{32}P$, fluorescent tags, chemiluminescent compounds, enzymes or other detectable labels known in the art.

One of the ways in which the anti-HNA antibody can be detectably labeled is by linking the same to an enzyme. The enzyme which is bound to the antibody will react with an appropriate substrate, preferably a chromogenic substrate, in such a manner as to produce a chemical moiety which can be detected, for example, by spectrophotometric or fluorimetric means. Enzymes which can be used to detectably label the antibodies but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme.

For example, the array containing target RNA hybridized thereto may be contacted with an anti-HNA antibody linked to an enzyme, e.g., alkaline-phosphatase, followed by incubation with a fluorescent alkaline phosphate substrate. For an illustrative example, see Section 6.2.1, infra.

It is also possible to label the antibodies with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

In another embodiment, a label other than a fluorescent label is used. For example, a radioactive label, or a pair of radioactive labels with distinct emission spectra, can be used (see Harlow, E. and Lane, D., 1988, "Antibodies: A Laboratory Manual", Cold Spring Harbor Laboratory Press, Cold Spring Harbor, N.Y.), which is incorporated herein by reference in its entirety. However, because of scattering of radioactive particles, and the consequent requirement for widely spaced binding sites, use of radioisotopes is a less-preferred embodiment.

The anti-HNA antibodies may be labeled before, during, or after contacting the array although in a preferred embodiment, the antibodies are labeled before contacting the array.

Alternatively to using labeled anti-HNA antibody to detect or measure anti-HNA antibody bound to heteroduplexes on the array (see infra), the antibody may be unlabeled and binding of the antibody to the heteroduplexes is detected by contacting the surface of the array with labeled antibody to the anti-HNA antibody. For example, if the anti-HNA antibody is human or murine antibody, labeled goat anti-human or goat anti-mouse antibody directed against the Fc portion of the anti-HNA antibody may be employed.

5.1.9 Binding of Anti-HNA Antibodies

The microarrays are contacted with anti-HNA antibodies under conditions such that immunospecific binding between the antibody and any heteroduplexes on the surface of the array can occur. Typically, a buffered (pH 7–9) physiological saline solution containing 0.1% bovine serum albumin is used.

5.1.10 Signal Detection and Data Analysis

When fluorescently labeled antibodies are used, the fluorescence emissions at each site of a transcript array can be, preferably, detected by scanning confocal laser microscopy. In a preferred embodiment, the arrays are scanned with a laser fluorescent scanner with a computer controlled X-Y stage and a microscope objective. Fluorescence laser scanning devices are described in Schena et al., 1996, *Genome Res.* 6:639–645 and in other references cited herein. Alternatively, the fiber-optic bundle described by Ferguson et al., 1996, *Nature Biotech.* 14:1681–1684, may be used to monitor mRNA abundance levels at a large number of sites simultaneously.

Signals are recorded and, in a preferred embodiment, analyzed by computer, e.g., using a 12 bit analog to digital board. In one embodiment the scanned image is despeckled using a graphics program (e.g., Hijaak Graphics Suite) and then analyzed using an image gridding program that creates a spreadsheet of the average hybridization at each wavelength at each site.

5.2 Applications

Because this invention achieves rapid and economical determination of the qualitative and quantitative presence of nucleic acids in a complex sample of nucleic acids, it has immediate application to problems relating to the genetic aspects of health and disease in human and other living species. In this application, the sample of nucleic acids is derived from biological sources according to protocols known in the art. For example, nucleic acids samples can include total cellular RNA, poly(A)$^+$ RNA, fractions of mRNA separated from subcellular compartments, infectious agent RNA, and so forth.

These naturally occurring nucleic acid samples can be derived from living sources of all types. The sources may be in vitro cell lines or cell populations, in vivo tissue samples, such as purified cell populations drawn or derived from wild-type occurrences or to tissue samples containing mixed cell populations, and so forth. The cells and tissues can be derived from all taxonomic classes, including viruses, bacteria and eukaryotes, prokaryotes, protista, plants, fungi, and animals of all phyla and classes. The animals can be vertebrates, mammals, primates, and especially humans. In particular, the animals can be laboratory animals used in research, such as mice or rats engineered or bred to have certain genomes or disease conditions or tendencies. The non-human sources can be subject to various exogenous factors, such as agents, stresses, treatments, and so forth, to determine the effect of such factors. Humans sources can be derived from clinical trials, pathological specimens, etc.

These applications can be generally divided into medical applications and research applications. Medical applications generally involve examination of known genes of known functions as part of diagnosis or treatment of a patient. Research applications generally involve expression analysis to detect novel genes, novel associations of genes, novel patterns of expression, and so forth.

In more detail, medical applications are of increasing importance as more and more diseases are recognized to have important genetic components to their etiology and development. Therefore, it is becoming increasingly useful to be able to assay the genetic makeup and expression of a tissue sample. For example, the expression of certain genes or their particular alleles can be prognostic or risk factors for disease (including disorders). Several examples of such diseases are found among the neuro-degenerative diseases, such as Parkinson's disease, Huntington's disease and ataxi-atelangiectasia. The origin or progression of several cancers, such as neuroblastoma, chronic lymphocytic leukemia and other B-cell malignancies, breast and ovarian cancer, and melanoma can now be linked to specific genetic defects (oncogenes and tumor suppressors being now widely known in the art). Finally, gene expression can also determine the presence and classification of foreign pathogens, especially those that might be difficult or impossible to culture in vitro but which nevertheless express their own unique genes.

Disease progression is reflected in changes in genetic expression of an affected tissue. For example, expression of particular tumor promoter genes and lack of expression of particular tumor suppressor genes is now known to correlate with the progression of certain tumors from normal tissue, to hyperplasia, to cancer in situ, and to metastatic cancer. Return of a cell population to a normal pattern of gene expression, such as by using anti-sense technology, can correlate with tumor regression. Therefore, knowledge of gene expression in a cancerous tissue can assist in staging and classifying this disease.

In this application, this invention can be used to compare broadly the expression of genomic sequences in two tissue sources at e.g., two different stages of disease progression or before and after a treatment.

Expression information can also be used to choose and guide therapy ("pharmacogenomics"). Accurate disease classification and staging or grading using gene expression information can assist in choosing initial therapies that are increasingly more tailored to the precise disease process occurring in the particular patient. Gene expression information can then track disease progression or regression, and such information can assist in monitoring the success or changing the course of an initial therapy. A therapy is favored that results in a regression towards normal or an abnormal pattern of gene expression in an individual, while therapy which has little effect on gene expression or its progression can need modification. Such monitoring is now useful for cancers and will become useful for an increasing number of other diseases, such as diabetes and obesity. Finally, in the case of direct gene therapy, expression analysis directly monitors the success of treatment. Expression differences in samples from tissue sources at different times, subject to different treatments, and so forth are assayed according to this invention as just described.

This invention is also applicable to samples of genomic DNA in a manner similar to its application to cDNA. Medical information of interest in genomic DNA samples includes occurrence and identity of translocations, gene amplifications, loss of heterozygosity for an allele, etc. This information is of interest in, for example, cancer diagnosis and staging or molecular genotyping to predict disease susceptibility and predisposition. In cancer patients, amplified sequences might reflect an oncogene, while loss of heterozygosity might reflect a tumor suppressor gene. Even without prior knowledge of the sequences of interest, detection and classification of patterns of nucleic acid expression is useful for the comparison of normal and diseased states or for observing the progression of a disease state. Gene expression information concerning the progression of a disease state is useful in order to elucidate the genetic mechanisms behind disease, to find useful diagnostic markers, to guide the selection and observe the results of therapies, etc.

In biological research, rapid and economical assay for gene expression in tissue or other samples has numerous applications. Such applications include, but are not limited to, for example, in pathology examining tissue specific genetic response to disease, in embryology determining developmental changes in gene expression, in pharmacology assessing direct and indirect effects of drugs on gene expression. Further, since an unknown sequence set pattern is indicative of an as yet unknown gene, this invention has important use for the discovery of new genes. Additionally, comparative gene-expression information can simplify discovery of detailed disease mechanisms. In medical research, by way of further example, use of the methods of this invention allow correlating gene expression with the presence and progress of a disease and thereby provide new methods of diagnosis and new avenues of therapy which seek to directly alter gene expression.

For example, certain cardiovascular tissues can be assayed from a normal laboratory animal and from a similar animal challenged by induced hypertension. Certain immune system tissues can be assayed from a normal animal and from a similar animal challenged with, e.g., bacterial endotoxins. Hepatic tissues can be assayed from a normal laboratory animal and one challenged with a drug or toxin. Tissues can be drawn from embryos at various stages and locations. Cell cultures and cell lines can also be sample sources. For example, samples can be derived from a "normal" cell culture and from the same cell culture subject to such factors as growth factors, signaling moieties, drugs and so forth.

Differences in expression are preferably deemed significant, e.g., when the difference in the genetic expression between two tissues exceeds the sum of the standard deviation of the expressions in the tissues. Other standard statistical comparisons as are known in the art can also be used to establish levels of expression and the significance of differences in levels of expressions.

For example, the relative abundance of an RNA in two cells or cell lines is scored as a perturbation and its magnitude determined (i.e., the abundance is different in the two sources of RNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation.

6. EXAMPLES

The invention is further described in the following examples which are in no way intended to limit the scope of the invention.

6.1 Materials and Methods 6.1.1 Preparation of a Microarray

In a specific embodiment, preparation of a microarray involves the steps of derivatizing the glass surface, preparing probes, and depositing the probes on the surface. Exemplary protocols for theses steps are presented in this subsection.

Derivatizing a Glass Surface

The protocols set forth herein describe preferred methods for preparing surfaces suitable for anchoring presynthesized probe nucleic acids. The protocols described produce preferred glass surfaces derivatized with covalently bound isothiocyanate groups.

1) Glass slides of 25×75×1 mm (Catalog # 12-552, Fisher Scientific, Pittsburgh, Pa.) were prewashed according to the following protocol.
   a) Slides were placed in a rack and washed with 5–6 changes of distilled water.
   b) Then they were soaked in 1 M NaOH for 4 hrs at room temperature, and rinsed with several changes of distilled water until the pH of the wash was close to 7.0.
   c) Slides were then soaked for 4 hrs to overnight in fuming nitric acid and rinsed again with dH2O until pH of the wash was 7.0.
   d) Slides were then air dried and stored in a vacuum desiccator.

2) The prewashed slides were used for surface modification according to the following steps
   a) Slides were immersed in 1% 3-aminopropyltrimethoxysilane (Aldrich Chemicals, Milwaukee, Wis.) solution in 95% acetone in water for 2 min.
   b) They were immediately transferred to a jar containing acetone, and washed with 10 changes of 5 min. each.
   c) The slides were then dried for 45 min in an oven set at 110° C.
   d) Slides were next immersed in 0.2% 1,4-phenylene diisothiocyanate ("PDC") solution (Sigma-Aldrich Chemicals, Milwaukee, Wis.) in 10% pyridine/dimethyl formamide for 2 hr with occasional stirring.
   e) The slides were washed with 3 changes of methanol followed by 3 changes of acetone for 10 min. each.
   f) Slides were air dried and stored in a vacuum desiccator.

Preparing Probes

Probes were synthesized by polymerase chain reaction (PCR) using primers specific for yeast open reading frames (ORFs) obtained from Research Genetics, Huntsville, Ala., according to manufacturer's instructions.

Depositing the Probes on the Glass Surface

Robotic methods were used to transfer the probe solutions onto the derivatized glass surface as described by Shena et al., 1996, *Proc. Natl. Acad. Sci. USA*, 93:10614 and DeRisi et al., 1997, Science, 278:680–686.

6.1.2 Preparation of a Target RNA

Methods for preparing total and poly(A)$^+$ RNA are well known and are described generally in Sambrook et al., supra. RNA was extracted from cells using guanidinium thiocyanate lysis followed by CsCl centrifugation (Chirgwin et al., 1979, *Biochemistry* 18:5294–5299). Poly(A)$^+$ RNA was selected by selection with oligo-dT cellulose (see Sambrook et al., supra). RNA was fragmented to a length of less than 150 bp by incubation at 60° C. for 0.5 hr with 1 mM $ZnCl_2$. EDTA was then added to a concentration of 10 mM.

6.1.3 Preparation of Labeled Anti-HNA Monoclonal Antibody

An alkaline phosphatase (AP)-conjugated anti-HNA monoclonal antibody/RNase mixture from a commercial anti-HNA-based kit purchased from Digene, Beltsville, Md. was used.

6.2 Hybridization Protocols

Microarrays were used for various hybridization tests described in this subsection.

6.2.1 Detection of DNA-RNA Hybridization on DNA Microarrays Using Anti-HNA mAb

The following example illustrates the ability of labeled anti-HNA mAb to detect RNA hybridization to DNA microarrays.

Figure 1:
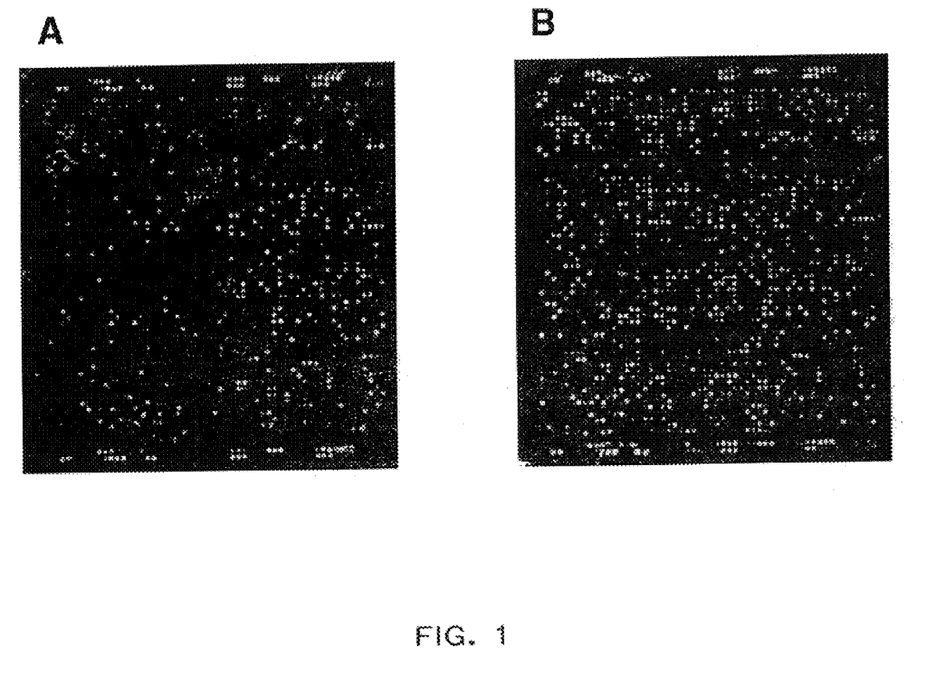
FIGS. 1A–1B. Detection of RNA hybridization to DNA microarrays using an alkaline phosphatase-conjugated anti-HNA monoclonal antibody. (A) Poly(A)⁺ RNA was hybridized with a DNA microarray on a glass microscope slide comprising approximately three thousand yeast genes (approximately one half of the genes in the yeast genome, called a 'half genome array'). (B) RNA, fragmented with $ZnCl_2$, was hybridized with a half genome array. Following hybridization, arrays were incubated with an alkaline phosphatase (AP)-conjugated anti-HNA monoclonal antibody/RNase mixture, followed by the fluorescent AP substrate, ELF-97. The arrays were scanned on a wide-field, optical sectioning microscope workstation. Images of fluorescence hybridization patterns were printed.

Poly(A)$^+$ RNA (2 μg) was hybridized for 16 hours at 60° C. with a DNA microarray on a glass microscope slide comprising approximately three thousand yeast genes (about one half of the genes in the yeast genome, called a 'half genome array') (FIG. 1A). In another experiment, RNA was fragmented to a length of less than 150 bp by incubation at 60° C. for 0.5 hr with 1 mM $ZnCl_2$. EDTA was then added to a concentration of 10 mM, and the fragmented RNA species were hybridized with a half genome array (FIG. 1B). Following hybridization, arrays were incubated with an AP-conjugated anti-HNA mAb/RNase mixture (described above in Section 6.1), followed by the fluorescent AP substrate, ELF-97 (Molecular Probes, Eugene, Oreg.). Glass coverslips were mounted over the arrays without allowing them to dry and arrays were scanned on a wide-field, optical sectioning microscope workstation (DeltaVision, Applied Precision, Inc., Issaquah, Wash.). Images of fluorescence hybridization patterns were printed from Photoshop (Adobe Photosystems, Seattle, Wash.).

The ability of an AP-conjugated anti-HNA Mab to detect RNA hybridization to DNA microarrays was evaluated. Labeled anti-HNA mAb detected hybridization of unfragmented poly(A)$^+$ RNA (FIG. 1A) and $Zn^{++}$-fragmented poly(A)$^+$ RNA, without enzymatic labeling of the samples.

Further, distinctive patterns of hybridization were observed when hybridization was detected with unfragmented poly(A)$^+$ RNA versus $Zn^{++}$-fragmented poly(A)$^+$ RNA. The difference in patterns of hybridization may be due to selective amplification of some hybridization signals by RNAs that have extensive secondary structures. Thus, a hybridizing RNA species that contains extensive secondary structures may bind more anti-HNA mAb molecules than one that does not. Hybridization patterns measured with fragmented RNAs, therefore, may more accurately represent transcript abundance.

6.2.2 Comparison of Hybridization Intensities: Labeled Anti-HNA mAb v. Labeled cDNA The following example illustrates the ability of labeled anti-HNA mAb to bind DNA-RNA hybrids at high levels of intensity.

Figure 2:
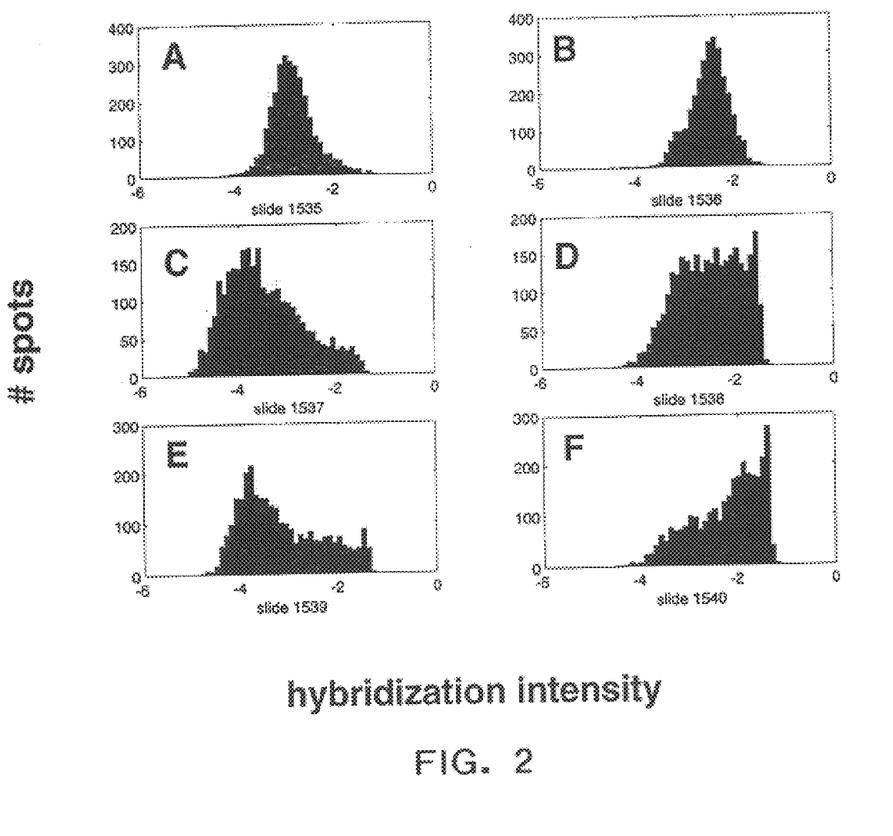
FIGS. 2A–2F. Comparison of hybridization intensities measured using cDNA mixtures labeled with fluorescent nucleotide with those detected using anti-HNA monoclonal antibody. Identical yeast half genome DNA microarrays were hybridized with: fluorescently-labeled cDNA (Cy3-labeled dUTP, Amersham, prepared as described by DeRisi et al., 1997, Science, 278:680–686 (FIGS. 2A–2B); unlabeled, unfragmented poly(A)$^+$ RNA (2 μg) (FIGS. 2C–2D); or unlabeled, Zn$^{++}$-fragmented poly(A)$^+$ RNA (2 μg) (FIGS. 2E–2F). Hybridization was performed at 42° C.

Hybridization intensities obtained with anti-HNA mAb were compared with those obtained using cDNA probes labeled with fluorescent nucleotides. Identical yeast half genome DNA microarrays were hybridized with: fluorescently-labeled cDNA (Cy3-labeled dUTP, Amersham, prepared as described by DeRisi et al., supra) (FIGS. 2A–2B); unlabeled, unfragmented poly(A)$^+$ RNA (2 μg) (FIGS. 2C–2D); or unlabeled, Zn$^{++}$-fragmented poly (A)$^+$ RNA (2 μg) (FIGS. 2E–2F). Hybridization was performed at 42° C. FIGS. 2A, 2C, and 2E) or 60° C. (FIGS. 2B, 2D, and 2F). Hybridization in FIGS. 2C–2F was detected with an AP-conjugated anti-HNA mAb and ELF-97 substrate, as described in Section 6.2.1. Hybridization intensities of different yeast ORFs were compared as histograms (FIGS. 2A–2F).

To evaluate the sensitivity of labeled anti-HNA mAb, the intensity of binding of labeled anti-HNA antibody to RNA hybridization on a DNA microarray was compared to intensity of binding of a labeled cDNA probe to a DNA microarray. All hybridizations were stronger at 60° C. than at 42° C. Hybridization intensities of different ORFs detected with Cy3-labeled cDNA samples varied over approximately a 100-fold range. In contrast, hybridization of different ORFs detected with anti-RNA mAb varied over a greater than 400-fold range. Thus, detection using anti-HNA mAb gave a greater dynamic range than that using Cy3-cDNA. In addition, hybridization intensities detected with anti-HNA mAb were stronger than those detected with Cy3-cDNA, such that under the conditions used, the intensities of many ORFs were off scale to the right. Thus, for detection of hybridization of polyA$^+$ RNA, anti-HNA mAb was more sensitive than fluorescently-labeled cDNA.

6.2.3 Detection of Total Cellular RNA Using Anti-HNA mAb

The following example illustrates the ability of labeled anti-HNA mAb to detect total cellular RNA hybridization to a DNA microarray.

Figure 3:
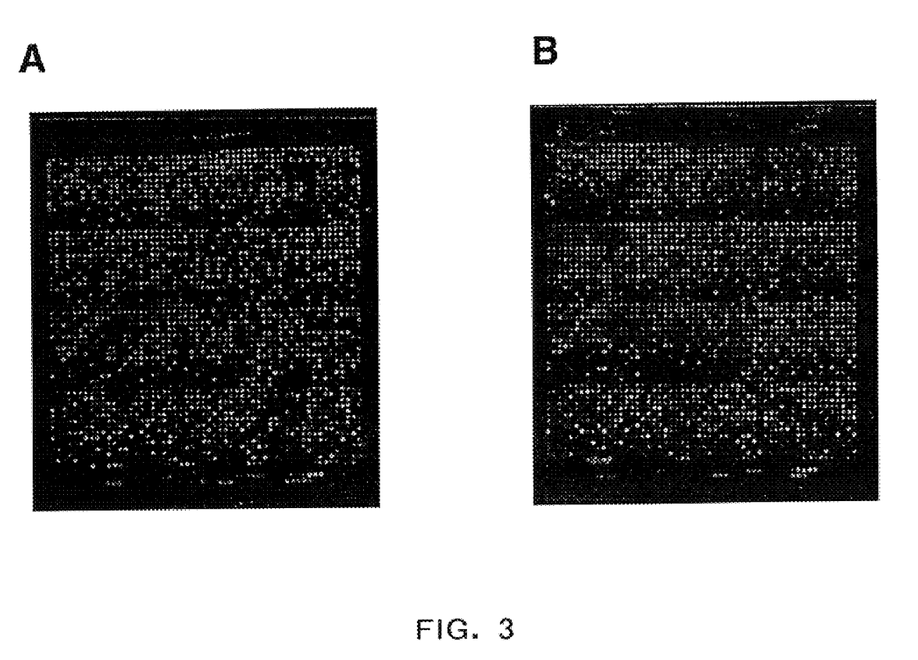
FIGS. 3A–3B. Detection of hybridization using total cellular RNA samples. Identical yeast half genome DNA microarrays were incubated with Zn$^{++}$-fragmented poly(A)$^+$ RNA (2 μg) (FIG. 3A) or with Zn$^{++}$-fragmented poly(A)$^+$ RNA total cellular RNA (10 μg) (FIG. 3B). Hybridization was detected with an AP-conjugated anti-HNA mAb and ELF-97 substrate, as in FIG. 1.

Identical yeast half genome DNA microarrays were incubated with Zn$^{++}$-fragmented poly(A)$^+$ RNA (2 μg) (FIG. 3A) or with Zn$^{++}$-fragmented poly(A)$^+$ RNA total cellular RNA (10 μg) (FIG. 3B). Hybridization was detected as described in Section 6.2.1.

The ability of labeled anti-HNA mAb to detect total cellular RNA was evaluated. The anti-HNA mAb detected strong hybridization when Zn$^{++}$-fragmented total yeast cellular RNA was incubated with a half genome array. This experiment demonstrates that anti-HNA mAb sensitively detected hybridization with total cellular RNA, thus obviating the need for isolation of the poly(A)$^+$ fraction.

7. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications and patent applications are cited herein, the disclosures of which are incorporated herein by reference in their entireties.

What is claimed is:

1. A method for detecting or measuring the amount of target RNA hybridized to an array of probe DNA or DNA mimics immobilized on a surface of a solid phase comprising:
   (a) contacting said array containing or suspected of containing target RNA hybridized thereto, with an antibody, said antibody being immunospecific to RNA-DNA or RNA-DNA mimic duplexes, under conditions such that immunospecific binding between said antibody and any RNA-DNA or RNA-DNA mimic duplexes on said surface can occur, wherein said probe DNA or DNA mimics provides hybridization sites at known, discrete locations on the surface of the solid phase for products of a plurality of genes and are at a density of greater than 60 probes per 1 cm$^2$; and
   (b) detecting or quantifying any binding of said antibody to said duplexes on said surface, wherein the presence or amount of antibody so bound indicates the presence or amount, respectively, of target RNA bound to probe DNA or DNA mimics on said surface.

2. The method according to claim 1 wherein the array is a microarray.

3. The method according to claim 1 wherein each probe comprises at least a portion of a gene.

4. The method according to claim 1 wherein each probe is 20 bases to 2000 bases.

5. The method according to claim 1 wherein each probe is 100 bases to 1000 bases.

6. The method according to claim 1 wherein each probe is 300 bases to 800 bases.

7. The method according to claim 1 wherein said probes are synthesized on the solid surface by photolithographic techniques.

8. The method according to claim 1 wherein said probes are printed onto the solid surface.

9. The method according to claim 1 wherein said target RNA is obtained from a cancer cell.

10. The method according to claim 1 wherein said target RNA is obtained from a cell exposed to a drug.

11. The method according to claim 1 wherein said antibody is labeled.

12. The method according to claim 11 wherein said antibody is labeled with a fluorescent compound, an enzymne, a chemiluminescent compound, or a radiolabel.

13. The method according to claim 1 wherein said antibody is a monoclonal antibody.

14. A method for detecting or measuring the amount of target RNA hybridized to an array of probe DNA or DNA mimics immobilized on a surface of a solid phase comprising:
   (a) contacting said target RNA with said probe DNA or DNA mimics on said array under conditions such that hybridization to form RNA-DNA or RNA-DNA mimic duplexes can occur, wherein said probe DNA or DNA mimics provides hybridization sites at known discrete locations on the surface of the solid phase for products of a plurality of genes and are at a density of greater than 60 probes per 1 cm$^2$;
   (b) contacting said array with an antibody, said antibody being immunospecific to RNA-DNA or RNA-DNA mimic duplexes, under conditions such that immunospecific binding between said antibody and any RNA-DNA or RNA-DNA mimic duplexes on said surface can occur; and
   (c) detecting or quantifying any binding of said antibody to said duplexes on said surface, wherein the presence or amount of antibody so bound indicates the presence or amount, respectively, of target RNA bound to probe DNA or DNA mimics on said surface.

15. A nucleic acid array comprising target RNA hybridized to an array of probe DNA or DNA mimics immobilized on a surface of a solid phase, which probe DNA or DNA mimics provides hybridization sites at known, discrete locations on the surface of the solid phase for products of a plurality of genes and are at a density of greater than 60 probes per 1 cm$^2$, wherein said hybridization results in the formation of RNA-DNA or RNA-DNA mimic duplexes, further comprising an antibody immunospecifically bound to said RNA-DNA or RNA-DNA mimic duplexes, said antibody being immunospecific to RNA-DNA or RNA-DNA mimic duplexes.

16. The nucleic acid array according to claim 15 wherein said antibody is a monoclonal antibody.

17. The nucleic acid array according to claim 15 where said antibody is labeled.

18. The nucleic acid array according to claim 17 wherein said antibody is labeled with an enzyme, chemiluminescent compound, fluorescent compound or radiolabel.

19. A kit comprising: (a) an array of probe DNA or DNA mimics immobilized on a surface of a solid phase, which probe DNA or DNA mimics provides hybridization sites at known, discrete locations on the surface of the solid phase for products of a plurality of genes and are at a density of greater than 60 probes per 1 cm$^2$; and (b) in a container, an antibody immunospecific to RNA-DNA or RNA-DNA mimic duplexes.

20. The kit according to claim 19 wherein said antibody is a monoclonal antibody.

21. The kit according to claim 19 wherein said antibody is labeled.

22. The kit according to claim 21 wherein said antibody is labeled with an enzyme, a chemiluminescent compound, a fluorescent compound, or a radiolabel.

23. The method according to claim 1 or 14 wherein the probe DNA or DNA mimics comprises a plurality of known, different sequences.

24. The method according to claim 23 wherein the DNA species are oligonucleotides.

25. The method according to claim 24 wherein the DNA species are oligonucleotides of less than 50 bases in length.

26. The method according to claim 24 wherein the DNA species are polynucleotides.

27. The method according to claim 24 wherein the DNA species are cDNA.

28. The method according to claim 1 or 15 wherein the target RNA is total cellular RNA from one or more cells.

29. The method according to claim 23 wherein the target RNA is total cellular RNA from one or more cells.

30. The method according to claim 1 or 14 wherein the target RNA is a plurality of distinct RNA species.

31. The method according to claim 23 wherein the target RNA is a plurality of distinct RNA species.

32. The method according to claim 1 or 14 wherein the level of abundance of target RNA is thereby quantitated.

33. The method according to claim 30 wherein the level of abundances of individual RNA species within said plurality is thereby quantitated.

34. The method according to claim 33 wherein the individual RNA species are less than 0.01% of the target RNA.

35. The method according to claim 34 wherein the individual RNA species are fragmented.

36. A method for detecting or measuring the amount of target RNA hybridized to an array of probe DNA or DNA mimics immobilized on a surface of a solid phase comprising:

(a) contacting said array containing or suspected of containing target RNA hybridized thereto, with a derivative of an antibody, said derivative containing the binding domain of the antibody said antibody being immunospecific to RNA-DNA or RNA-DNA mimic duplexes, under conditions such that immunospecific binding between said derivative and any RNA-DNA or RNA-DNA mimic duplexes on said surface can occur, wherein said probe DNA or DNA mimics provides hybridization sites at known, discrete locations on the surface of the solid phase for products of a plurality of genes and are at a density of greater than 60 probes per 1 cm$^2$; and (b) detecting or quantifying any binding of said derivative to said duplexes on said surface, wherein the presence or amount of derivative so bound indicates the presence or amount, respectively, of target RNA bound to probe DNA or DNA mimics on said surface.

37. A method for detecting or measuring the amount of target RNA hybridized to an array of probe DNA or DNA mimics immobilized on a surface of a solid phase comprising:

(a) contacting said target RNA with said probe DNA or DNA mimics on said array under conditions such that hybridization to form RNA-DNA or RNA-DNA mimic duplexes can occur, wherein said probe DNA or DNA mimics provides hybridization sites at known, discrete locations on the surface of the solid phase for products of a plurality of genes and are at a density of greater than 60 probes per 1 cm$^2$;

(b) contacting the surface of said array with a derivative of an antibody, said derivative containing the binding domain of the antibody, said derivative being immunospecific to RNA-DNA or RNA-DNA mimic duplexes, under conditions such that immunospecific binding between said derivative and any RNA-DNA or RNA-DNA mimic duplexes on said surface can occur; and (c) detecting or quantifying any binding of said derivative to said duplexes on said surface, wherein the presence or amount of derivative so bound indicates the presence or amount, respectively, of target RNA bound to probe DNA or DNA mimics on said surface.

38. A nucleic acid array comprising target RNA hybridized to one or more probe DNA or DNA mimics within an array of probe DNA or DNA mimics immobilized on a surface of a solid phase, which probe DNA or DNA mimics provides hybridization sites at known, discrete locations on the surface of the solid phase for products of a plurality of genes and are at a density of greater than 60 probes per 1 cm$^2$, wherein said hybridization results in the formation of RNA-DNA or RNA-DNA mimic duplexes; further comprising a derivative of an antibody, said derivative containing the binding domain of the antibody, said antibody being immunospecific to RNA-DNA or RNA-DNA mimic duplexes.

39. A kit comprising: (a) an array of probe DNA or DNA mimics immobilized on a surface of a solid phase, which DNA or DNA mimics provides hybridization sites at known, discrete locations on the surface of the solid phase for products of a plurality of genes and are at a density of greater than 60 probes per 1 cm$^2$; and (b) in a container, a derivative of an antibody said derivative containing the binding domain of the antibody, said antibody being immunospecific to RNA-DNA or RNA-DNA mimic duplexes.

40. A method for detecting or measuring the amount of target DNA hybridized to an array of probe RNA immobilized on a surface of a solid phase comprising:

(a) contacting said array containing or suspected of containing target DNA hybridized thereto, with an antibody, said antibody being immunospecific to RNA-DNA duplexes, under conditions such that immunospecific binding between said antibody and any RNA-DNA duplexes on said surface can occur; and (b) detecting or quantifying any binding of said antibody to said duplexes on said surface, wherein the presence or amount of antibody so bound indicates the presence or amount, respectively, of target DNA bound to probe RNA on said surface.

41. A method for detecting or measuring the amount of arget DNA hybridized to an array of probe RNA immobilized on surface of a solid phase comprising:

(a) contacting said target DNA with said probe RNA on said array under conditions such that hybridization to form RNA-DNA duplexes can occur;

(b) contacting the surface of said array with an antibody, said antibody being immunospecific to RNA-DNA duplexes, under conditions such that immunospecific binding between said antibody and any RNA-DNA duplexes on said surface can occur; and (c) detecting or quantifying any binding of said antibody to said duplexes on said surface, wherein the presence or amount of antibody so bound indicates the presence or amount, respectively, of target DNA bound to probe RNA on said surface.

42. A nucleic acid array comprising target DNA hybridized to one or more probe RNA within an array of probe RNA immobilized on a surface of a solid phase to form RNA-DNA duplexes, further comprising an antibody immunospecifically bound to said RNA-DNA duplexes, said antibody being immunospecific to RNA-DNA duplexes.

43. A kit comprising: (a) an array of probe RNA immobilized on a surface of a solid phase; and (b) in a container an antibody immunospecific to RNA-DNA duplexes.

44. A method for detecting or measuring the amount of target DNA hybridized to an array of probe RNA immobilized on a surface of a solid phase comprising:

(a) contacting said array containing or suspected of containing target DNA hybridized thereto, with a derivative of an antibody, said derivative containing the binding domain of the antibody, said antibody being immunospecific to RNA-DNA duplexes, under conditions such that immunospecific binding between said derivative and any RNA-DNA duplexes on said surface can occur; and (b) detecting or quantifng any binding of said derivative to said duplexes on said surface, wherein the presence or amount of derivative so bound indicates the presence or amount, respectively, of target DNA bound to probe RNA on said surface.

45. A method for detecting or measuring the amount of target DNA hybridized to an array of probe RNA immobilized on a surface of a solid phase comprising:

(a) contacting said target DNA with said probe DNA or DNA mimics on said array under conditions such that hybridization to form RNA-DNA duplexes can occur;

(b) contacting the surface of said array with a derivative of an antibody, said derivative containing the binding domain of the antibody, said derivative being immunospecific to RNA-DNA duplexes, under conditions such that immunospecific binding between said derivative and any RNA-DNA duplexes on said surface can occur; and (c) detecting or quantifying any binding of said derivative to said duplexes on said surface, wherein the presence or amount of derivative so bound indicates the presence or amount, respectively, of target DNA bound to probe RNA on said surface.

46. A nucleic acid array comprising target DNA hybridized to one or more probe RNA within an array of probe RNA immobilized on a surface of a solid phase to form RNA-DNA duplexes, further comprising a derivative of an antibody, said derivative containing the binding domain of the antibody immunospecifically bound to said RNA-DNA duplexes, said derivative being immunospecific to RNA-DNA duplexes.

47. A kit comprising: (a) an array of probe RNA immobilized on a surface of a solid phase; and (b) in a container a derivative of an antibody, said derivative containing the binding domain of the antibody, said derivative being immunospecific to RNA-DNA duplexes.

48. The method according to claim 1, 14, 36, 37, 40, 41, 44, or 45 wherein said array comprises greater than 1,000 different nucleic acid probes and the density of said different nucleic acid probes is greater than 1,000 per $cm^2$.

49. A method of expression analysis of a cell comprising:

(a) contacting a population of RNA isolated from said cell with an array of probe DNA or DNA mimics, wherein the probe DNA or DNA mimics is immobilized on a surface of a solid phase under conditions such that hybridization to form RNA-DNA or RNA-DNA mimic duplexes can occur, wherein said probe DNA or DNA mimics provides hybridization sites at known, discrete locations on the surface of the solid phase for products of a plurality of genes and are at a density of greater than 60 probes per 1 $cm^2$;

(b) contacting said array with an antibody, said antibody being immunospecific to RNA-DNA or RNA-DNA mimic duplexes, under conditions such that immunospecific binding between said antibody and any RNA-DNA or RNA-DNA mimic duplexes on said surface can occur; and (c) detecting or quantifying any binding of said antibody to said duplexes on said surface, wherein the presence or amount of antibody so bound indicates the presence or amount, respectively, of target RNA bound to probe DNA or DNA mimics on said surface.

50. The method according to claim 1, 14, 36, 37, or 49 wherein the plurality of genes are of the genome of a cell or organism.

51. The method according to claim 50, wherein the plurality of genes comprises at least 50% of the genes in the genome of said cell or organism.

52. The method according to claim 50, wherein the plurality of genes comprises at least 75% of the genes in the genome of said cell or organism.

53. The method according to claim 50, wherein the plurality of genes comprises at least 90% of the genes in the genome of said cell or organism.

54. The method according to claim 50, wherein the plurality of genes comprises at least 99% of the genes in the genome of said cell or organism.

55. The method according to claim 50, wherein the genome is the human genome.

56. The method according to claim 50, wherein the genome is the yeast genome.

57. The method according to claim 1, 14, 36, 37, or 49, wherein the array comprises at least 100 different probes.

58. The method according to claim 1, 14, 36, 37, or 49, wherein the array comprises at least 1000 different probes.

59. The method according to claim 1, 14, 36, 37, or 49, wherein the array comprises at least 5,000 probes.

60. The method according to claim 1, 14, 36, 37, or 49, wherein the probe density is greater than 500 probes per 1 cm$^2$.

61. The method according to claim 1, 14, 36, 37, or 49, wherein the probe density is greater than 1,000 probes per 1 cm$^2$.

62. The method according to claim 1, 14, 36, 37, or 49, wherein the probe density is greater than 2,000 probes per 1 cm$^2$.

63. The method according to claim 1, 14, 36, 37, or 49, wherein the array is less than 6.25 cm$^2$ in size.

64. The method according to claim 63, wherein the array is at least 1.6 cm$^2$ in size.

65. The kit according to claim 19 or 39, wherein the plurality of genes are of the genome of a cell or organism.

66. The kit according to claim 65, wherein the plurality of genes comprises at least 50% of the genes in the genome of said cell or organism.

67. The kit according to claim 65, wherein the plurality of genes comprises at least 75% of the genes in the genome of said cell or organism.

68. The kit according to claim 65, wherein the plurality of genes comprises at least 90% of the genes in the genome of said cell or organism.

69. The kit according to claim 65, wherein the plurality of genes comprises at least 99% of the genes in the genome of said cell or organism.

70. The kit according to claim 65, wherein the genome is the human genome.

71. The kit according to claim 65, wherein the genome is the yeast genome.

72. The kit according to claim 19 or 39, wherein the array comprises at least 100 different probes.

73. The kit according to claim 19 or 39, wherein the array comprises at least 1,000 different probes.

74. The kit according to claim 19 or 39, wherein the array comprises at least 5,000 different probes.

75. The kit according to claim 19 or 39, wherein the probe density is greater than 500 probes per 1 cm$^2$.

76. The kit according to claim 19 or 39, wherein the probe density is greater than 1,000 probes per 1 cm$^2$.

77. The kit according to claim 19 or 39, wherein the probe density is greater than 2,000 probes per 1 cm$^2$.

78. The kit according to claim 19 or 39, wherein the array is less than 6.25 cm$^2$ in size.

79. The kit according to claim 19 or 39, wherein the array is at least 1.6 cm$^2$ in size.

80. The nucleic acid array according to claim 15 or 38, wherein the plurality of genes are of the genome of a cell or organism.

81. The nucleic acid array according to claim 80, wherein the plurality of genes comprises at least 50% of the genes in the genome of said cell or organism.

82. The nucleic acid array according to claim 80, wherein the plurality of genes comprises at least 75% of the genes in the genome of said cell or organism.

83. The nucleic acid array according to claim 80, wherein the plurality of genes comprises at least 90% of the genes in the genome of said cell or organism.

84. The nucleic acid array according to claim 80, wherein the plurality of genes comprises at least 99% of the genes in the genome of said cell or organism.

85. The nucleic acid array according to claim 80, wherein the genome is the human genome.

86. The nucleic acid array according to claim 80, wherein the genome is the yeast genome.

87. The nucleic acid array according to claim 15 or 38, wherein the array comprises at least 100 different probes.

88. The nucleic acid array according to claim 15 or 38, wherein the array comprises at least 1,000 different probes.

89. The nucleic acid array according to claim 15 or 38, wherein the array comprises at least 5,000 different probes.

90. The nucleic acid array according to claim 15 or 38, wherein the probe density is greater than 500 probes per 1 cm$^2$.

91. The nucleic acid array according to claim 15 or 38, wherein the probe density is greater than 1,000 probes per 1 cm$^2$.

92. The nucleic acid array according to claim 15 or 38, wherein the probe density is greater than 2,000 probes per 1 cm$^2$.

93. The nucleic acid array according to claim 15 or 38, wherein the array is less than 6.25 cm$^2$ in size.

94. The nucleic acid array according to claim 93, wherein the array is at least 1.6 cm$^2$ in size.

95. The method according to claim 40, 41, 44 or 45, wherein said probe RNA provides hybridization sites at known, discrete locations on the surface of the solid phase for cDNA of products of a plurality of genes and are at a density of greater than 60 probes per 1 cm$^2$.

96. The nucleic acid array according to claim 42 or 46, wherein said probe RNA provides hybridization sites at known, discrete locations on the surface of the solid phase for cDNA of products of a plurality of genes and are at a density of greater than 60 probes per 1 cm$^2$.

97. The kit according to claim 43 or 47, wherein said probe RNA provides hybridization sites at known, discrete locations on the surface of the solid phase for cDNA of products of a plurality of genes and are at a density of greater than 60 probes per 1 cm$^2$.

98. The method according to claim 1, wherein the plurality of genes comprises at least 50% of the genes in the genome of a cell or organism, wherein the probe density is greater than 1,000 probes per 1 cm$^2$.

* * * * *